US012491124B2

(12) United States Patent
Newkirk et al.

(10) Patent No.: US 12,491,124 B2
(45) Date of Patent: Dec. 9, 2025

(54) MEDICAL EQUIPMENT STATUS INDICATOR

(71) Applicant: Hill-Rom Services, Inc., Batesville, IN (US)

(72) Inventors: David Newkirk, Lawrenceburg, IN (US); Eric R. Meyer, Batesville, IN (US); Brian Guthrie, Greensburg, IN (US); Brandon Fisk, Brookville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 693 days.

(21) Appl. No.: 16/794,899

(22) Filed: Feb. 19, 2020

(65) Prior Publication Data

US 2020/0268580 A1 Aug. 27, 2020

Related U.S. Application Data

(60) Provisional application No. 62/810,565, filed on Feb. 26, 2019.

(51) Int. Cl.
*A61G 7/057* (2006.01)
*A47G 21/10* (2006.01)
(Continued)

(52) U.S. Cl.
CPC .............. *A61G 7/057* (2013.01); *A61B 5/742* (2013.01); *A47G 21/10* (2013.01); *A61B 5/7435* (2013.01);
(Continued)

(58) Field of Classification Search
CPC ...... A47G 21/10; A61G 7/057; A61G 7/0506; A61G 7/05; A61G 2203/16; A61G 2203/20; A61B 5/742; A61B 5/7435
See application file for complete search history.

(56) References Cited

U.S. PATENT DOCUMENTS 1,760,346 A * 5/1930 Correa ................ A47C 21/022 24/72.5
1,929,657 A * 10/1933 Sinclair ................ A47C 21/022 24/72.5
(Continued)

FOREIGN PATENT DOCUMENTS

EP 2777670 A1 9/2014
WO 2007008831 A2 1/2007
(Continued)

OTHER PUBLICATIONS

Schurter, "Configurable Input Device CDS1," 8pgs., Accessed from the Internet on Dec. 21, 2018, https://www.schurter.com/en/Landing-Page/Products-and-Technologies/CDS1.

*Primary Examiner* — Matthew Troutman
*Assistant Examiner* — Morgan J McClure
(74) *Attorney, Agent, or Firm* — Price Heneveld LLP

(57) ABSTRACT

A mattress state indicator includes a housing. The mattress state indicator also includes a display supported by the housing. The display is configured to provide visual indicia of a mattress operation state of a mattress. The display includes a light source disposed proximate the display. A connection feature is engaged with the housing. The connection feature is configured to couple the housing with a bed.

3 Claims, 16 Drawing Sheets

(51) Int. Cl.
*A61B 5/00* (2006.01)
*A61G 7/05* (2006.01)

(52) U.S. Cl.
CPC .............. *A61G 7/05* (2013.01); *A61G 7/0506* (2013.01); *A61G 2203/16* (2013.01); *A61G 2203/20* (2013.01)

(56) References Cited

U.S. PATENT DOCUMENTS

| | | | | | |
|---|---|---|---|---|---|
| 1,948,965 | A * | 2/1934 | Hart | A47C 21/022 24/72.5 |
| 3,757,363 | A * | 9/1973 | Langlais | A47C 21/003 248/314 |
| 3,781,843 | A * | 12/1973 | Harrison | G08B 7/04 200/83 Z |
| 3,929,309 | A * | 12/1975 | De Vore | A47C 1/10 5/652 |
| 3,981,492 | A * | 9/1976 | Hallmann | A61B 6/0421 5/81.1 R |
| 4,346,298 | A * | 8/1982 | Dixit | A61B 6/04 5/601 |
| 4,616,813 | A * | 10/1986 | McConnell | A61G 13/10 5/658 |
| 4,913,413 | A * | 4/1990 | Raab | A61G 13/12 5/624 |
| 4,968,078 | A * | 11/1990 | Fitzwater | B25B 5/06 D8/395 |
| 5,335,651 | A * | 8/1994 | Foster | A61B 50/13 5/503.1 |
| 5,349,340 | A * | 9/1994 | Blumenthal | G08B 7/06 340/321 |
| 5,404,602 | A * | 4/1995 | Kondo | A47C 21/022 24/514 |
| 5,934,721 | A * | 8/1999 | Walde | A47J 43/283 294/7 |
| 6,014,346 | A * | 1/2000 | Malone | G04F 1/005 600/595 |
| 6,023,800 | A * | 2/2000 | Stickley | A61G 7/0507 5/503.1 |
| 6,295,670 | B1 * | 10/2001 | Schieberl | A47C 21/022 24/72.5 |
| 7,027,358 | B1 * | 4/2006 | Esposito | G04F 8/08 600/592 |
| 7,458,622 | B2 * | 12/2008 | Tardif | A47J 43/283 294/99.2 |
| 7,719,437 | B2 * | 5/2010 | Bertram, III | F21V 21/096 362/396 |
| 7,850,302 | B1 * | 12/2010 | Riazi | G02C 3/04 351/158 |
| 8,051,515 | B1 * | 11/2011 | Kring | A61G 13/101 5/503.1 |
| 8,146,599 | B2 * | 4/2012 | Wilson | A61B 90/57 128/845 |
| 8,621,692 | B1 * | 1/2014 | Kring | A61G 13/101 5/503.1 |
| 8,833,707 | B2 * | 9/2014 | Steinberg | A61G 13/102 248/101 |
| 9,149,211 | B2 * | 10/2015 | Mravyan | A61G 5/1043 |
| 10,034,679 | B1 * | 7/2018 | Boyer | A61B 17/8872 |
| 10,912,524 | B2 * | 2/2021 | Al-Ali | A61B 5/0205 |
| 11,013,652 | B1 * | 5/2021 | Miller | A61G 13/125 |
| 11,058,240 | B2 * | 7/2021 | Bearden | A61B 5/6892 |
| 2002/0101311 | A1 * | 8/2002 | May, III | B25B 11/002 335/205 |
| 2005/0172389 | A1 * | 8/2005 | Herbst | E03D 5/08 4/405 |
| 2006/0059630 | A1 * | 3/2006 | Romano | A61G 7/05769 5/706 |
| 2006/0157996 | A1 * | 7/2006 | McRorie, III | A47G 21/10 294/16 |
| 2011/0030141 | A1 * | 2/2011 | Soderberg | A61H 23/04 5/600 |
| 2011/0169653 | A1 * | 7/2011 | Wang | A61G 7/012 340/686.6 |
| 2014/0103183 | A1 * | 4/2014 | Lokhande | B62D 33/07 248/352 |
| 2014/0313700 | A1 * | 10/2014 | Connell | F21V 33/0012 362/130 |
| 2014/0345058 | A1 * | 11/2014 | Escobedo | A61G 5/1043 5/655.3 |
| 2015/0257952 | A1 * | 9/2015 | Zerhusen | A61G 7/0514 340/12.5 |
| 2016/0135731 | A1 * | 5/2016 | Drennan | A61B 5/746 600/587 |
| 2017/0202361 | A1 * | 7/2017 | White | A47C 21/022 |
| 2017/0330430 | A1 * | 11/2017 | Goodfield | A61G 7/05 |
| 2018/0192780 | A1 * | 7/2018 | Lowe | A47C 21/022 |
| 2018/0353358 | A1 * | 12/2018 | Lingegård | A61G 7/012 |
| 2018/0369039 | A1 * | 12/2018 | Bhimavarapu | A61G 7/0507 |
| 2019/0008708 | A1 * | 1/2019 | Moreno | A61G 7/005 |
| 2019/0015276 | A1 * | 1/2019 | Bhimavarapu | H02J 7/0042 |
| 2019/0060143 | A1 * | 2/2019 | Archambault | A61G 5/1097 |
| 2019/0209806 | A1 * | 7/2019 | Allen | H04L 12/2829 |
| 2019/0350318 | A1 * | 11/2019 | Levine | A47K 10/02 |
| 2020/0032989 | A1 * | 1/2020 | Genenbacher | F21V 21/088 |
| 2020/0405580 | A1 * | 12/2020 | Rok | A61J 9/008 |

FOREIGN PATENT DOCUMENTS

| | | | |
|---|---|---|---|
| WO | 2016123595 | A1 | 8/2016 |
| WO | 2017093549 | A1 | 6/2017 |

* cited by examiner

MEDICAL EQUIPMENT STATUS INDICATOR

CROSS-REFERENCE TO RELATED APPLICATION

This application claims priority to and the benefit under 35 U.S.C. § 119(e) of U.S. Provisional Application No. 62/810,565, filed on Feb. 26, 2019, entitled "MEDICAL EQUIPMENT STATUS INDICATOR," the disclosure of which is hereby incorporated herein by reference in its entirety.

FIELD OF THE DISCLOSURE

The present disclosure generally relates to a medical equipment status indicator, and more specifically to a medical equipment status indicator for use with a mattress to provide indication of a mattress operation state.

SUMMARY OF THE DISCLOSURE

According to one aspect of the present disclosure, a mattress state indicator includes a housing. The mattress state indicator also includes a display supported by the housing. The display is configured to provide visual indicia of a mattress operation state of a mattress. The display includes a light source disposed proximate the display. A connection feature is engaged with the housing. The connection feature is configured to couple the housing with a bed.

According to another aspect of the present disclosure, a mattress state indicator includes a housing. A display is supported by the housing and is configured to provide visual indicia of a mattress operation state of a mattress. The display includes a light source disposed proximate the display. A bracket is engaged with the housing and includes a clamp that applies a compressive force against a portion of a bed.

According to yet another aspect of the present disclosure, a mattress state indicator assembly includes a housing and a display that provides visual indicia of an operation state of a mattress. The display communicates wirelessly with a controller of a bed that controls the operation state of the mattress. A connector is disposed within the housing and engages a complementary connector disposed within the bed.

These and other features, advantages, and objects of the present invention will be further understood and appreciated by those skilled in the art by reference to the following specification, claims, and appended drawings.

DETAILED DESCRIPTION

Figure 1A:
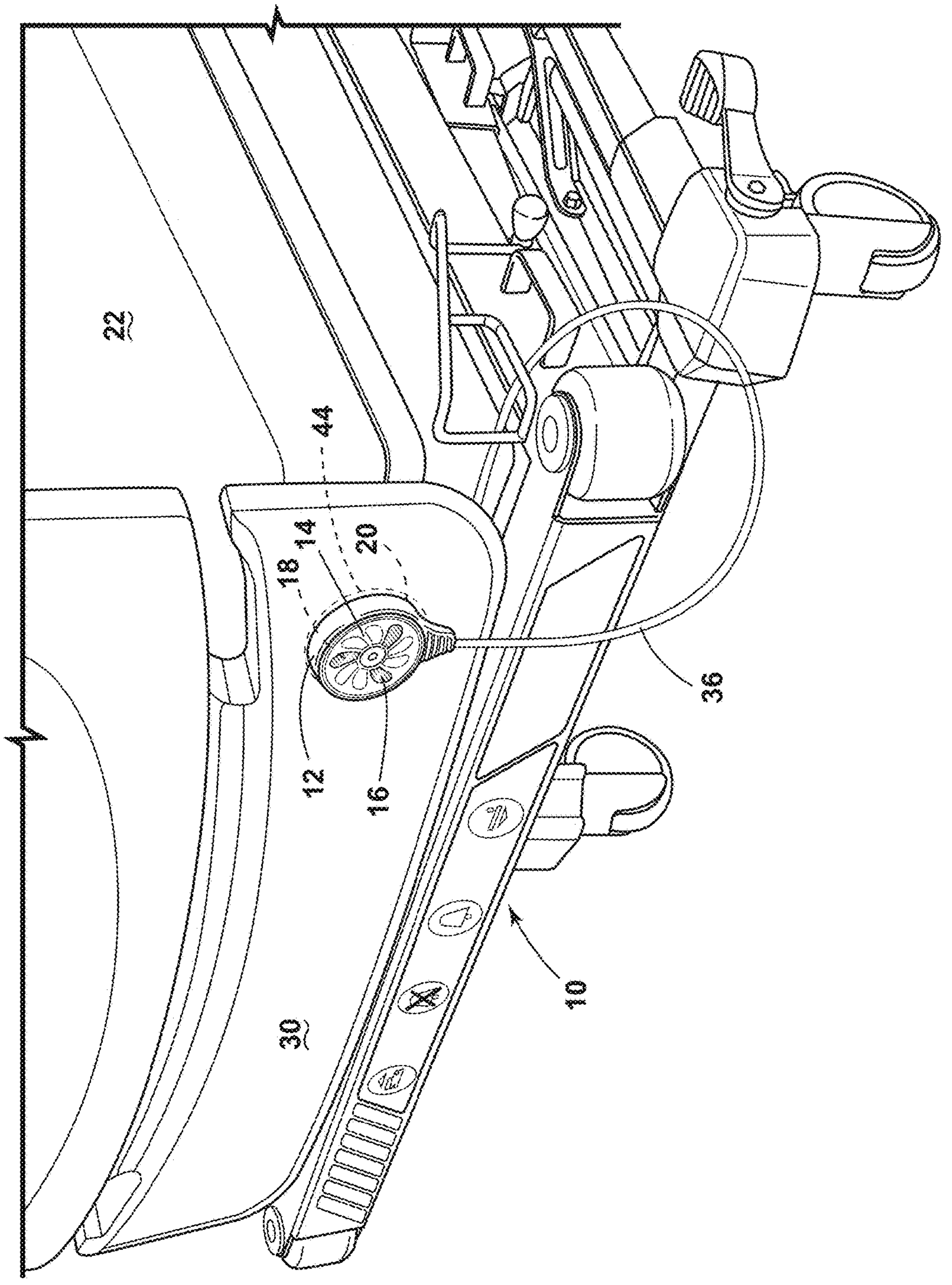
FIG. 1A is a top perspective view of a medical equipment status indicator removably coupled with a footboard of a hospital bed.
Figure 1B:
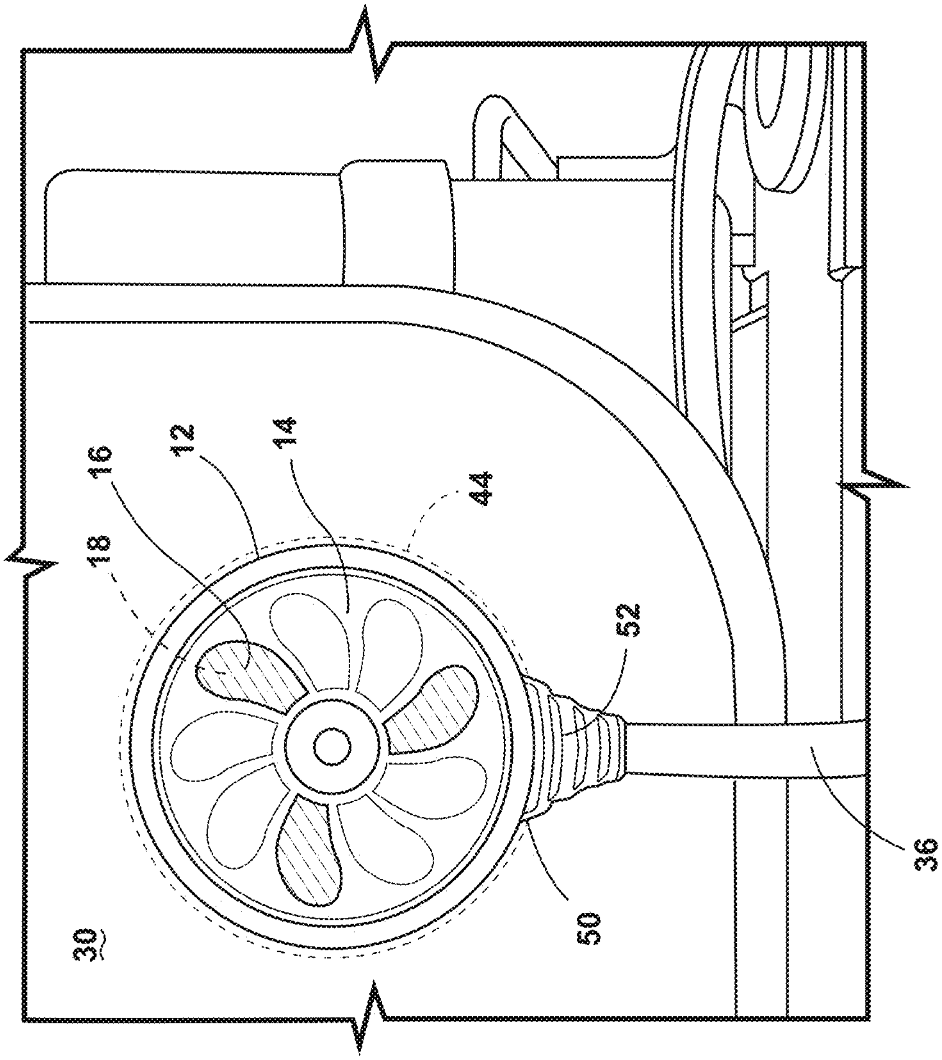
FIG. 1B is a front elevational view of a medical equipment status indicator of the present disclosure.

For purposes of description herein, the terms "upper," "lower," "right," "left," "rear," "front," "vertical," "horizontal," and derivatives thereof, shall relate to the disclosure as oriented in FIG. 1A. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1A-11, reference numeral 10 generally designates a medical equipment status indicator in the form of a mattress state indicator including a housing 12. The mattress state indicator 10 also includes a display 14 supported by the housing 12. The display 14 is configured to provide visual indicia 16 of a mattress operation state of a mattress. The display 14 includes a light source 18 disposed proximate the display 14. A connection feature 20 is engaged with the housing 12. The connection feature 20 is configured to couple the housing 12 with a bed 22, such as a hospital bed.

With reference again to FIGS. 1A and 1B, the mattress state indicator 10 is configured for use with the hospital bed 22 to provide a quick and efficient visual indication to a caregiver of an operation status of the mattress of the hospital bed 22. It is generally contemplated that the mattress state indicator 10 will provide visual confirmation of an operation state that may include client management features, such as micro-climate management. It is generally contemplated that visual indication of the operation state of the hospital bed 22 can be provided, without the need for interactive interfaces such as buttons or switches. With the mattress state indicator 10 attached to the hospital bed 22, caregivers can confirm the proper operation of the mattress frequently in order to maximize effective use of the mattress and reduce the likelihood of skin breakdown, which could lead to lesions or sores. Additionally, caregivers should be able to view the operation state of the mattress from an easily viewable location such as a footboard 30. To that end, the mattress state indicator 10 should be positioned in a location that is visually non-obstructive and that does not interfere with other forms of patient care. The mattress state indicator 10 may be operably coupled with any portion of the hospital bed 22, however, in FIG. 1A, the mattress state indicator 10 is illustrated as being operably coupled with the footboard 30 above a frame 32 of the hospital bed 22. The mattress state indicator 10 may be coupled with the hospital bed 22 via various attachment methods. For example, the mattress state indicator 10 may be magnetically coupled with the footboard 30 of the hospital bed 22 by a magnetic member (another magnet or a metal that attracts a magnet). The mattress state indicator 10 in conjunction with a complementary connection feature on a hospital bed 22 defines a mattress state indicator assembly.

With reference now to FIGS. 1A-2C, the mattress state indicator 10 may also be attached to a cord 36 that allows the mattress state indicator 10 to be placed on either side of the footboard 30 without dragging the cord 36 on the floor. The cord 36 provides electrical communication (power and/or data) between the display 14 and a controller of the bed 22. However, it is also contemplated that the display 14 may communicate wirelessly with the controller that is configured to adjust the mattress operation state. A magnet 40 is disposed inside the housing 12 of the mattress state indicator 10 and has a first side 42 that is attached to a magnetic feature in the form of a metal disk or complementary magnet 44. It is generally contemplated that the first side 42 of the magnet 40 may include a polarity that is opposite that of the complementary magnet 44. The magnetic feature may be adhesively attached to the footboard 30 or mounted with a mechanical fastener to the footboard 30 of the bed 22. Alternatively, the magnetic feature may be embedded in the footboard 30 during manufacturing of the footboard 30. In this instance, an indicia or symbol may be disposed on an external surface of the footboard 30 to indicate where the magnetized feature is embedded within the footboard 30. Other methods for connection are set forth herein.

The mattress state indicator 10 includes the display 14 that may be illuminated to provide the visual indicia 16 associated with the operation state of the mattress. The display 14 may include a variety of light sources, such as light emitting diodes (LEDs). The LEDs may be designed to operate with multiple circuits such that the LEDs may provide the appearance of motion, flashing, color, etc. In addition, the LEDs may be side-lit so as to reduce the overall thickness of the mattress state indicator 10 thereby providing a lean, aesthetically pleasing profile. It will be understood that the mattress state indicator 10 may be easily removed from the footboard 30 of the bed 22 to allow repositioning, cleaning, etc.

With reference again to FIGS. 2A-2C, a peripheral portion 50 of the housing 12 may include a molded-in strain relief member 52 to minimize excessive strain where electrical and data wiring enters the housing 12 of the mattress state indicator 10. Although the housing 12 is shown with a circular construction, it will also be understood that the housing 12 may take on a variety of other constructions, including square, rectangular, etc.

Figure 2A:
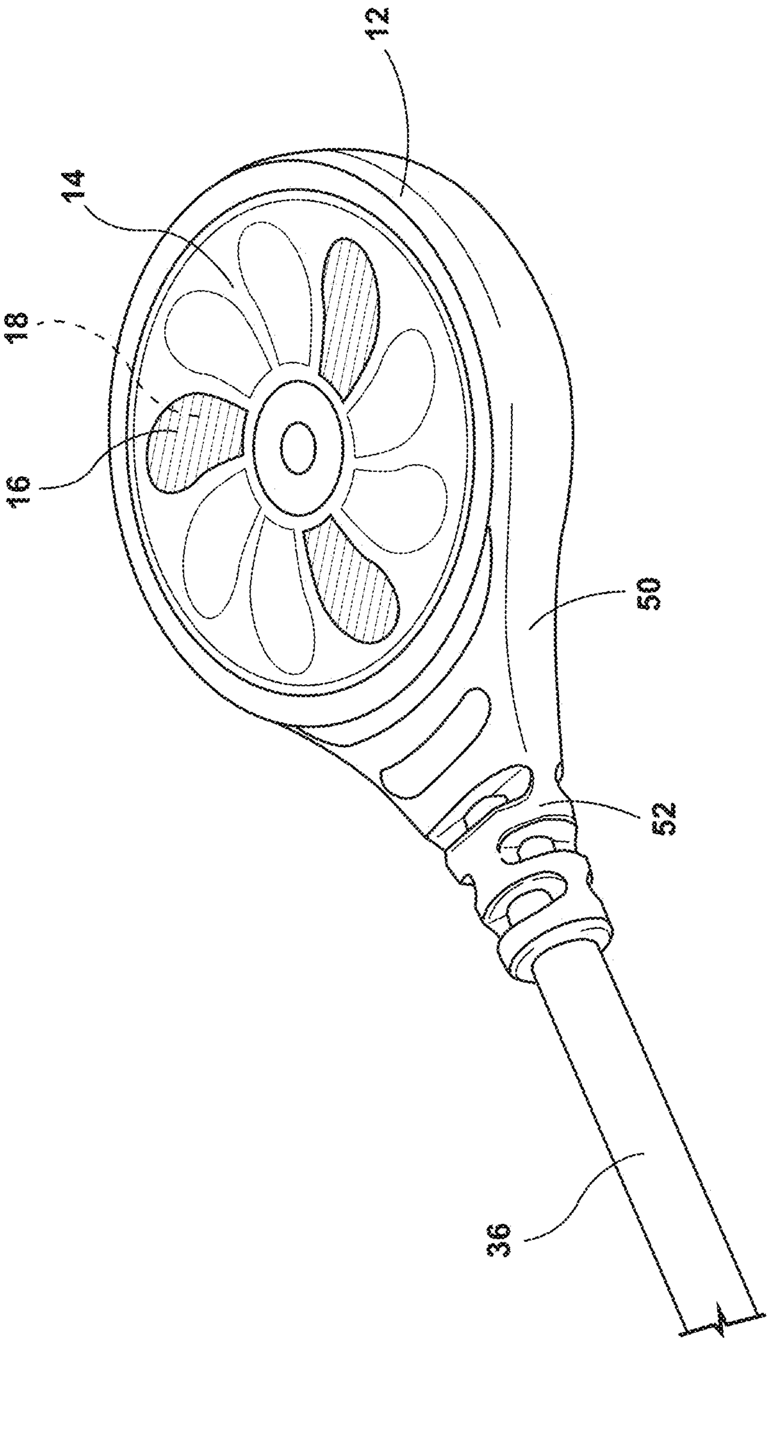
FIG. 2A is a top perspective view of a medical equipment status indicator, of the present disclosure, prior to engagement with a hospital bed.
Figure 2B:
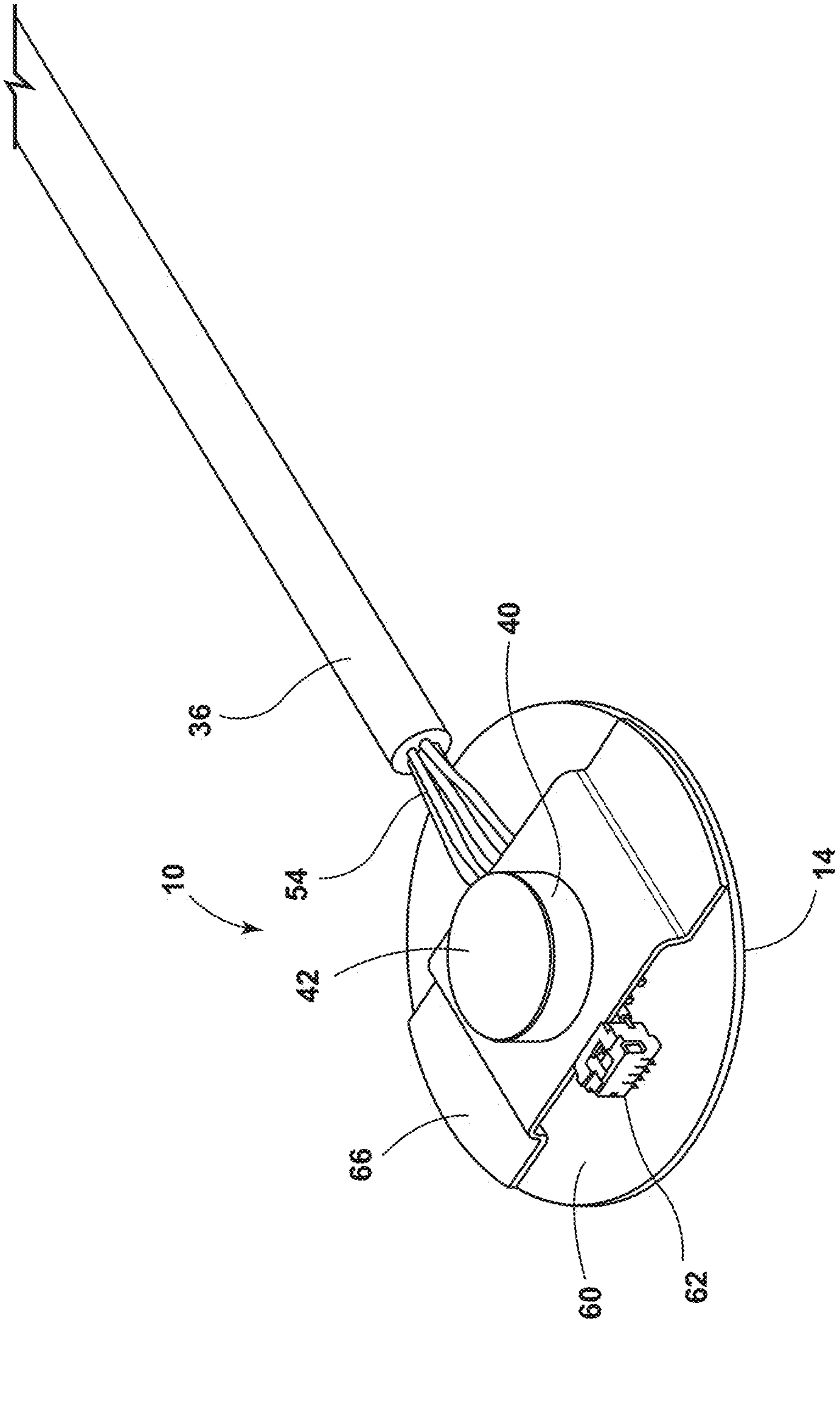
FIG. 2B is a top perspective view of a medical equipment status indicator, of the present disclosure, with a housing of the medical equipment status indicator removed.
Figure 2C:
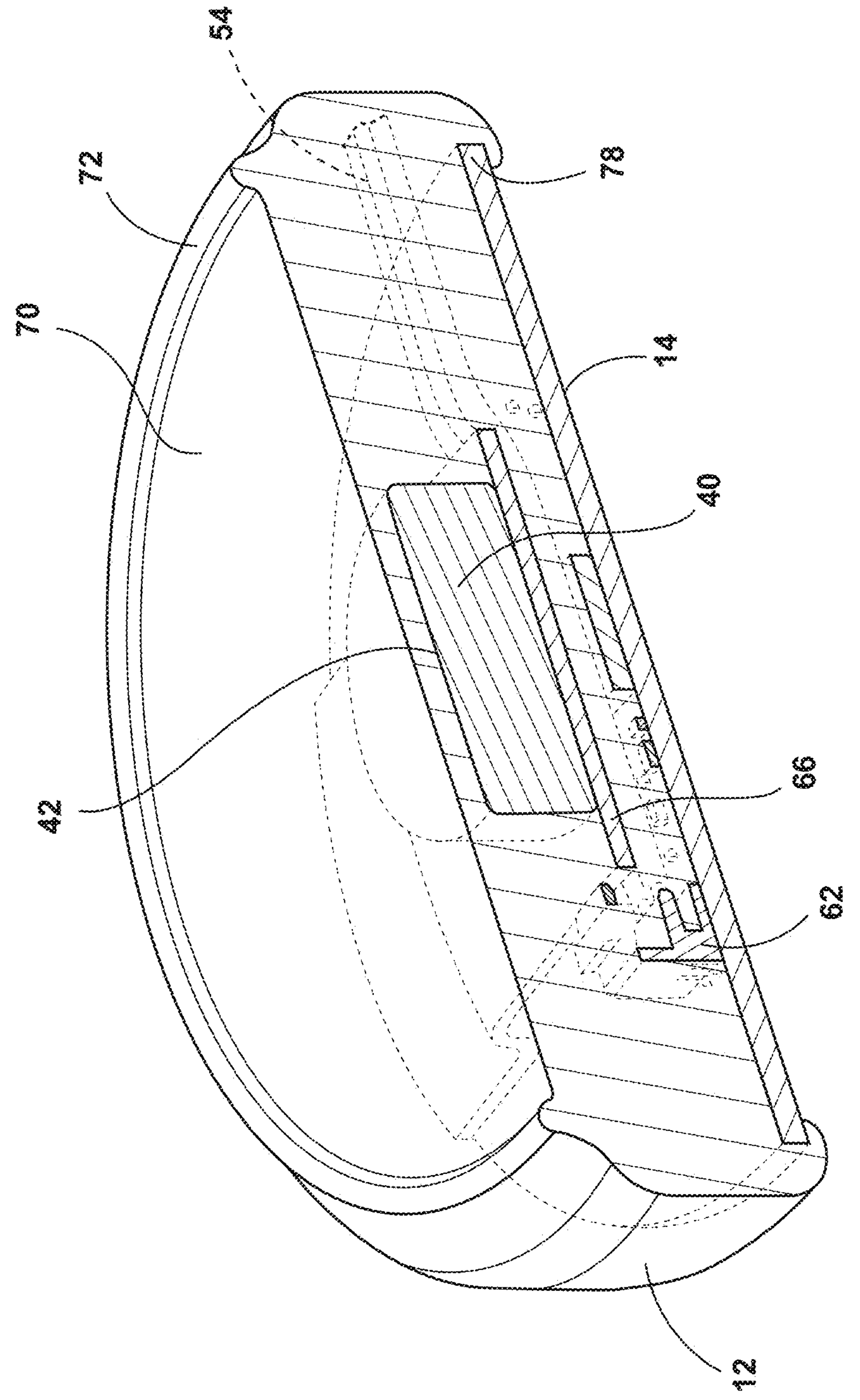
FIG. 2C is an enlarged top perspective cross-sectional view of a medical equipment status indicator of the present disclosure.

With reference again to FIG. 2B, the mattress state indicator 10 is illustrated with the housing 12 removed. The cord 36 is shown with wiring 54 that provides electrical communication to a printed circuit board (PCB) 60 by way of an electrical plug 62. In the construction of FIG. 2B, the wiring 54 extends past the magnet 40 such that the electrical plug 62 is disposed on an opposite side of the mattress state indicator 10 than where the wiring 54 enters the mattress state indicator 10. The electrical plug 62 may provide power or data to the PCB 60 or both power and data to the PCB 60 of the mattress state indicator 10. The PCB 60 is operably coupled with the display 14, which as previously noted, may include a variety of light sources. In addition, a back side of the PCB 60 includes a bracket 66. The bracket 66 is operably coupled with the magnet 40 which is disposed within the housing 12. The bracket 66 may support the magnet 40 and also act as a radio frequency (RF) shield for the PCB 60. The magnet 40 is configured for magnetically securing the mattress state indicator 10 to a complementary magnetized feature of the hospital bed 22. As previously noted, the magnetized feature may be a metal plate, or may be another magnet 44 with a pole opposite to that of the first side 42 of the magnet 40, such that the magnet 44 and the first side 42 are attracted to one another. Further, the magnetized feature may be disposed interior to or exterior to a portion of the hospital bed 22.

With reference again to FIG. 2C, the magnet 40 is clearly disposed adjacent to a rear surface 70 of the housing 12. The rear surface 70 may be surrounded by a peripheral rim 72 configured to receive a metal plate (FIG. 4A) that is magnetically attached to the magnet 40 adjacent the rear surface 70. In this case, the peripheral rim 72 serves as a locating feature that properly locates the housing 12 against a metal plate or metal plate location on the hospital bed 22. In addition, it can be seen that the display 14 includes an outer edge 78 that is over-molded by the housing 12. Accordingly, the housing 12 protects the outer edge 78 of the display 14 from damage.

Figure 3B:
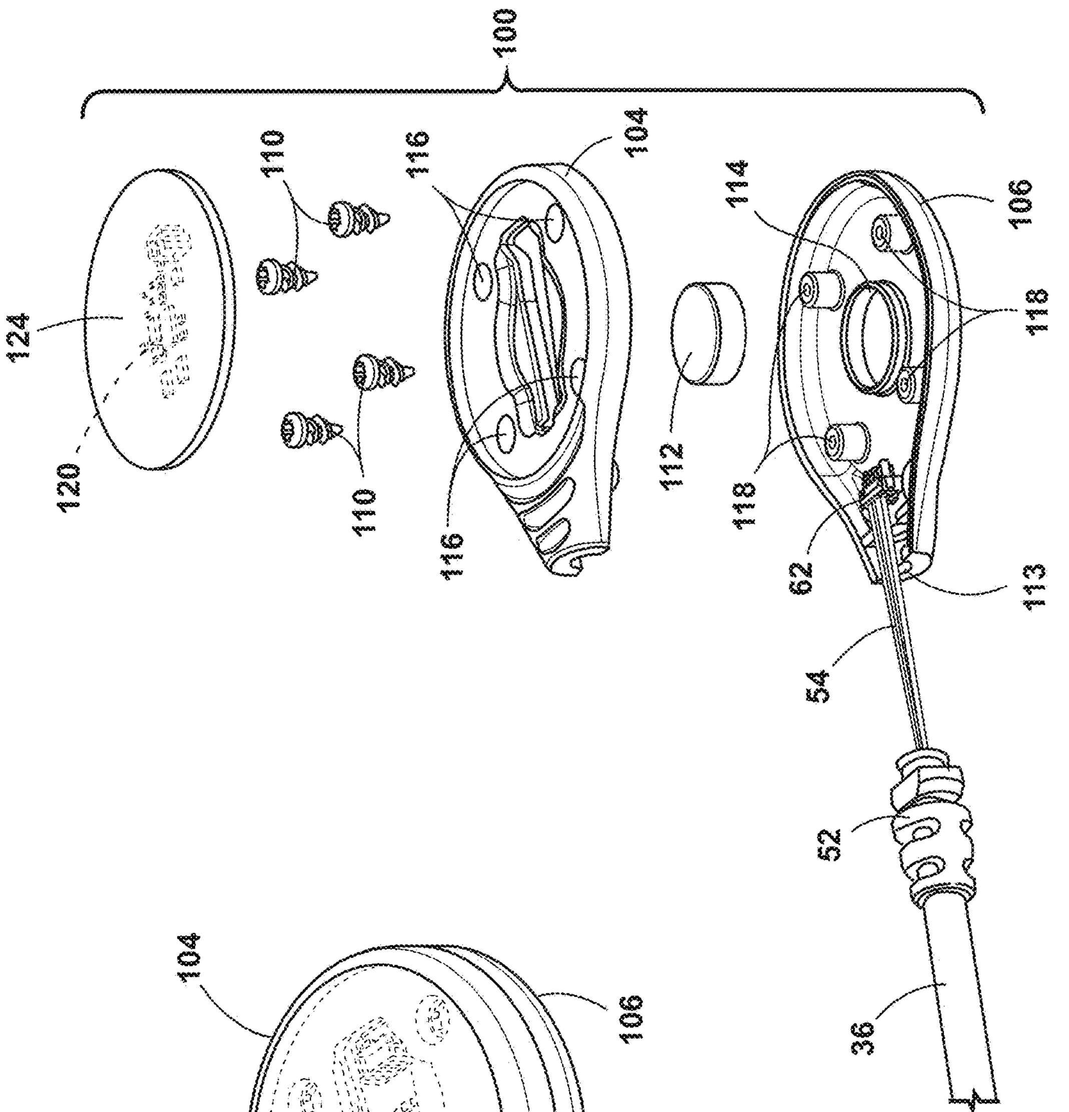
FIG. 3B is a top perspective exploded view of a medical equipment status indicator of the present disclosure.
Figure 3A:
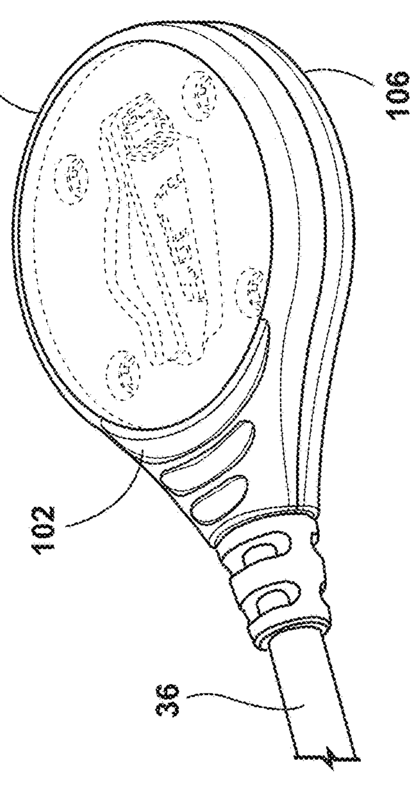
FIG. 3A is a top perspective view of a medical equipment status indicator, of the present disclosure, prior to placement of a display thereon.

With reference now to FIGS. 3A and 3B, in another aspect of the present disclosure, a mattress state indicator 100 includes a housing 102 having a clamshell type configuration. The clamshell configuration includes a first housing portion 104 that is operably coupled to a second housing portion 106 by mechanical fasteners 110. The mechanical fasteners 110 extend through receiving apertures 116 and are securely received into bosses 118. In this instance, the wiring 54 does not extend past the magnet 112, but instead is proximate an opening 113 of the housing 102. A magnet 112 is disposed in the second housing portion 106 and is located within an internal ring 114 that properly locates the magnet 112 relative to the second housing portion 106. After the first housing portion 104 and the second housing portion 106 are mechanically connected, and the magnet 112 is secured within the internal ring 114, the electrical plug 62, which is in electrical communication with the wiring 54, can be inserted into the housing 102 and coupled with circuitry 120 that is operably coupled with a display 124. The display 124 is secured to the first housing portion 104. The display 124 may be secured by adhesive, for example. It will be understood that the display 124 includes the same or similar features as the display 14 as set forth herein.

Figure 4A:
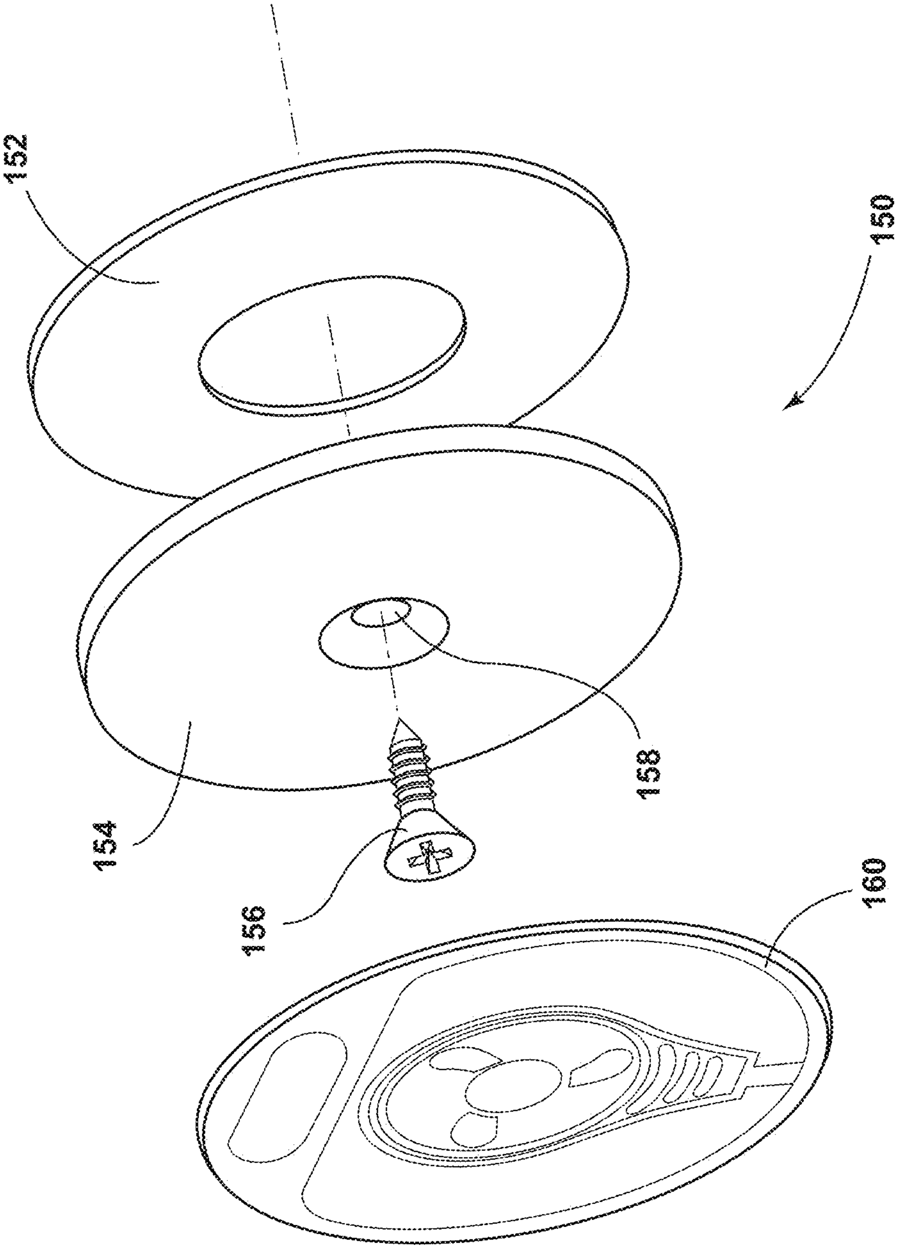
FIG. 4A is a side perspective exploded view of a medical equipment status indicator, of the present disclosure, prior to installation.

It is generally contemplated, regardless of the construction of the mattress state indicator, that the mattress state indicator will be operably coupled with the hospital bed 22. In one instance, as shown in FIG. 4A, a connection feature 150 includes an adhesive ring 152 that acts as an interface between a metal plate 154 (which, alternatively, could be a complementary magnet) and the footboard 30 of the hospital bed 22. A mechanical fastener 156 extends through a fastener aperture 158 in the metal plate 154 and a label or decal 160 is positioned over the metal plate 154. This construction is configured to interface with the magnet 40 of the mattress state indicator 10 or the magnet 112 of the mattress state indicator 100. The mechanical fastener 156 secures the metal plate 154 to the footboard 30 and the adhesive ring 152 prevents rotation of the metal plate 154 relative to the footboard 30.

Figure 4B:
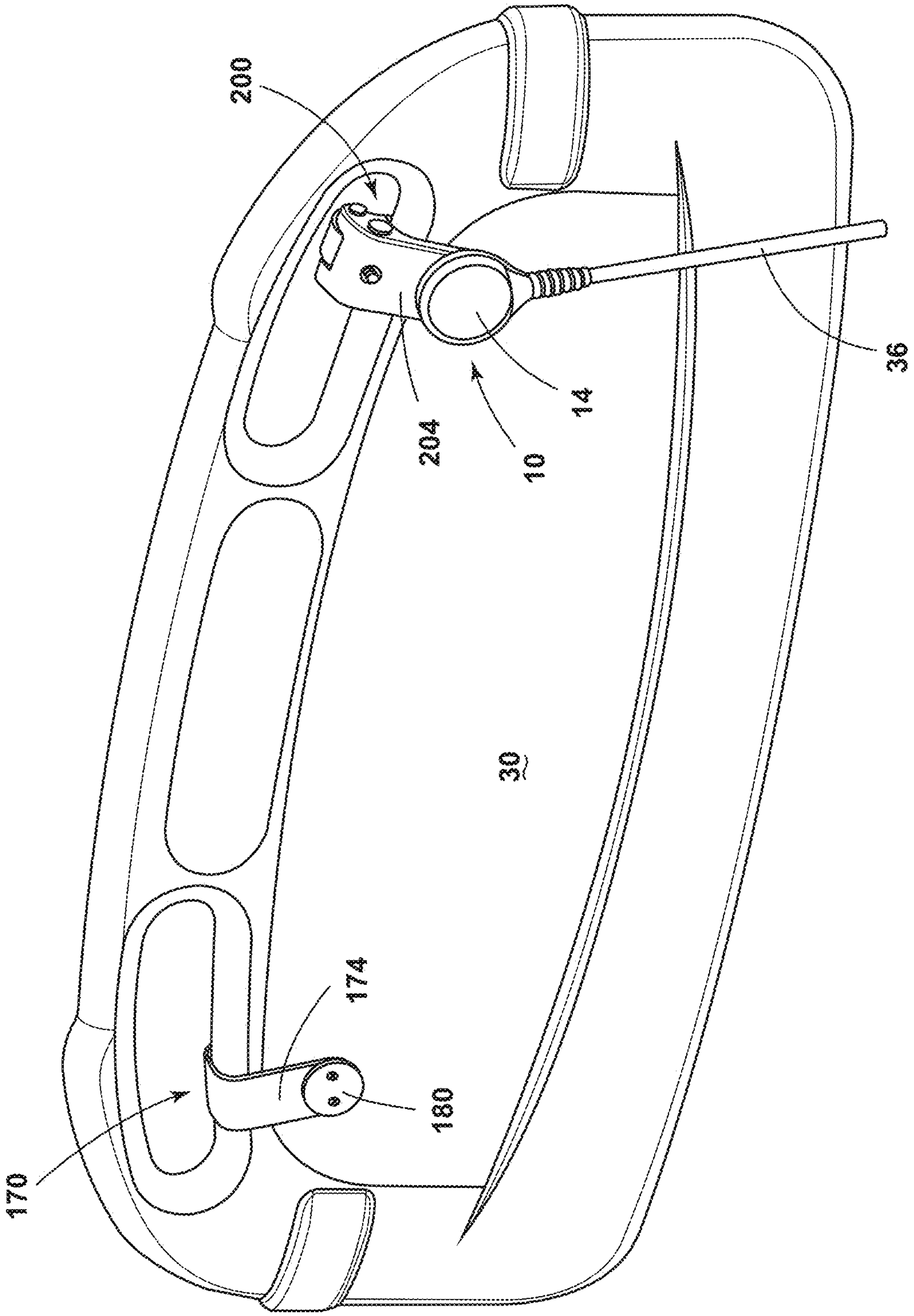
FIG. 4B is a top perspective view of a footboard of a hospital bed illustrating various connection features for securing a medical equipment status indicator to the footboard.

With reference now to FIG. 4B, the mattress state indicator 10 may also be secured to the footboard 30 by less permanent coupling assemblies. The coupling assemblies may include clamps that are secured to a portion of the footboard 30 or other areas of the hospital bed 22. In these instances, the clamps may be removed from the hospital bed 22 quickly and easily, without permanently marking or damaging the hospital bed 22.

Figure 5B:
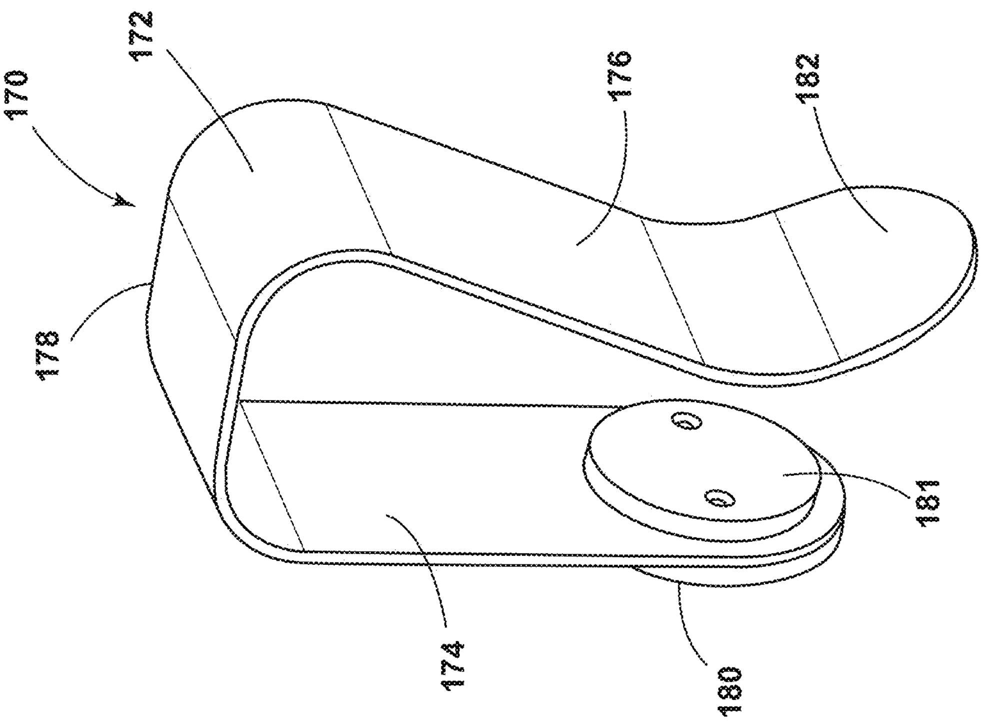
FIG. 5B is a rear perspective view of a clamp used to secure a medical equipment status indicator to a hospital bed.
Figure 5A:
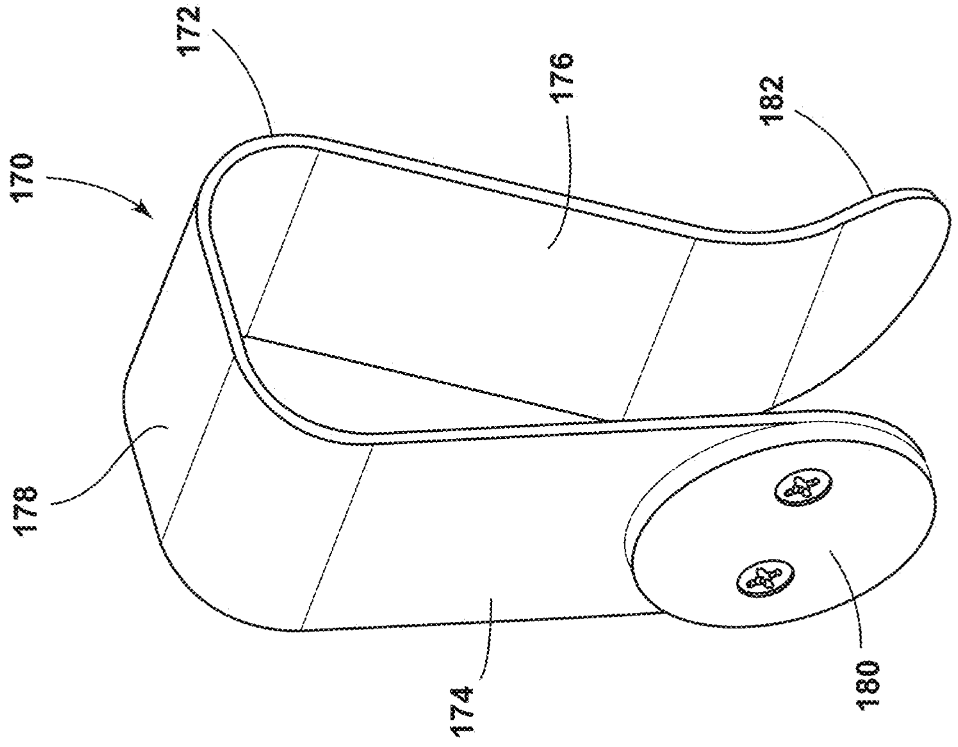
FIG. 5A is a front perspective view of a clamp used to secure a medical equipment status indicator to a hospital bed.

With reference now to FIGS. 5A and 5B, an instance of a connection feature 170 in the form of a bracket is illustrated. The connection feature 170 illustrates a spring steel clamp 172 including first and second arms 174, 176 that are operably coupled by an intermediate portion 178. An outside surface of the first arm 174 includes a metal plate 180, or any other known magnetic member, configured to interface with the magnet 40 of the mattress state indicator 10 or the magnet 112 of the mattress state indicator 100. An inside surface of the first arm 174 includes a pliable engagement member 181 made of a highly frictional polymer, for example, that assists in frictionally securing the connection feature 170 to a portion of the hospital bed 22. The second arm 176 is turned slightly inward and includes a spring biased arrangement configured to frictionally engage a portion of the hospital bed 22, such as the footboard 30. Thus, the spring steel claim is configured to apply a compressive force against a portion of the hospital bed 22. A bottom end 182 of the second arm 176 defines an outwardly extending tab configured to allow a caregiver to pull the second arm 176 away from the first arm 174, thereby releasing the spring steel clamp 172 from the hospital bed 22. The spring steel clamp 172 can then be relocated or moved to a different hospital bed 22. The space between the first and second arms 174, 176 is generally smaller than engagement areas (such as the footboard 30, for example) of the hospital bed 22.

Figure 6A:
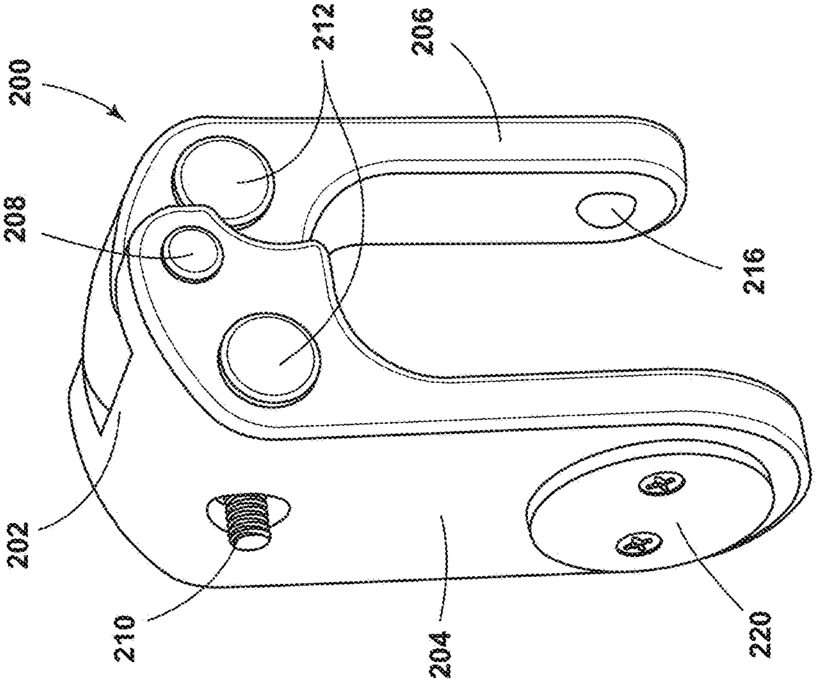
FIG. 6A is a front perspective view of another clamp used to secure a medical equipment status indicator to a hospital bed.
Figure 6B:
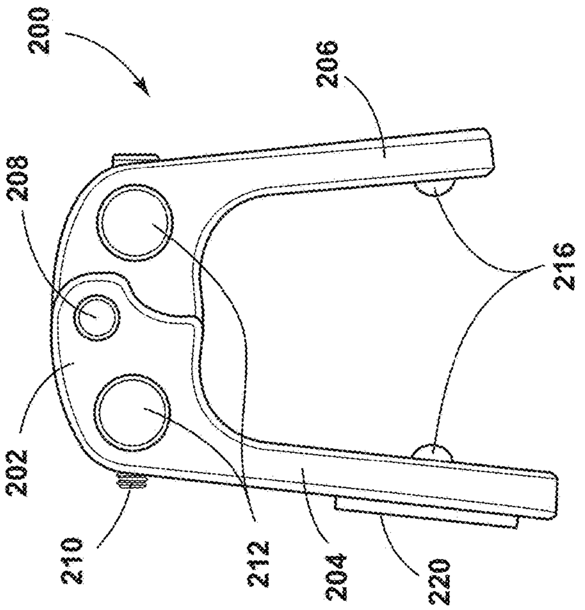
FIG. 6B is a side elevational view of a clamp used to secure a medical equipment status indicator to a hospital bed.
Figure 6C:
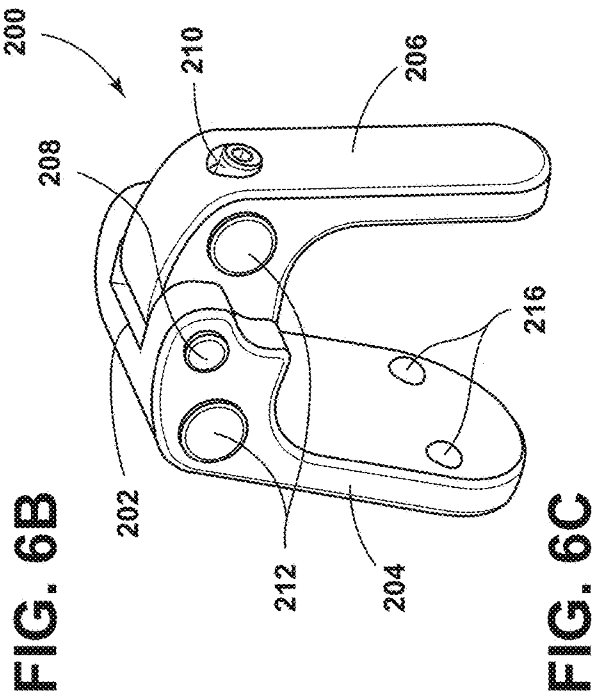
FIG. 6C is a rear perspective view of another clamp used to secure a medical equipment status indicator to a hospital bed.

With reference now to FIGS. 6A-6C, another connection feature 200 in the form of a bracket is illustrated, which includes an adjustable clamp 202, which may be constructed from a polymeric material such as plastic. The adjustable clamp 202 includes first and second downwardly extending arms 204, 206 that are operably coupled by a pivot pin 208. The pivot pin 208 allows for the first and second downwardly extending arms 204, 206 to rotate relative to one another. A threaded engagement member in the form of a threaded bolt 210 extends through first and second threaded dowels 212 disposed inside each of the first and second downwardly extending arms 204, 206. The first and second threaded dowels 212 may be made from a variety of materials such as, for example, metal. The threaded bolt 210 may be tightened, by a tool or by hand, such that the adjustable clamp 202 tightly engages the hospital bed 22. An inside surface of each of the first and second downwardly extending arms 204, 206 may include a pliable material 216 configured to engage the hospital bed 22 without placing undue stress on either the adjustable clamp 202 or the hospital bed 22. In addition, a metal plate 220, or other magnetic member, is disposed on an outside surface of the first downwardly extending arm 204 and is configured for interface with the magnet 40 of the mattress state indicator 10 or the magnet 112 of the mattress state indicator 100.

Figure 7B:
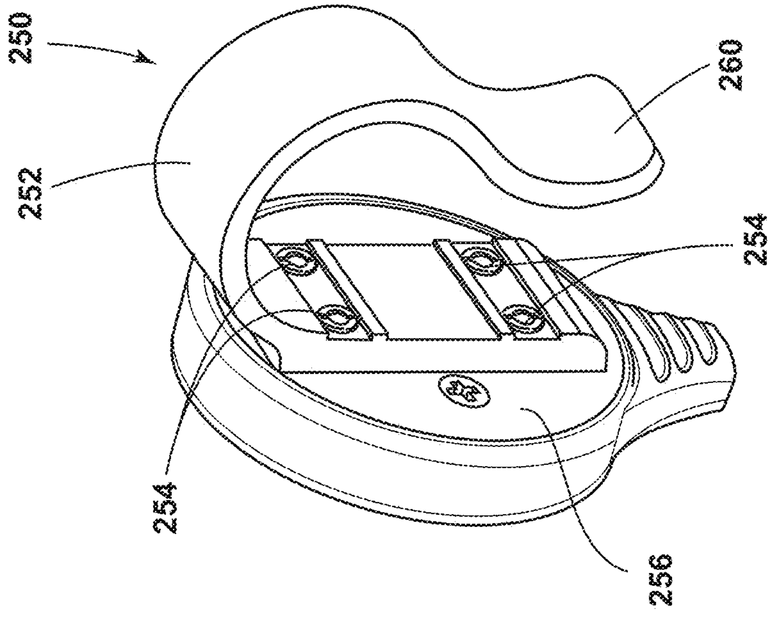
FIG. 7B is a top rear perspective view of another connection feature for a medical equipment status indicator of the present disclosure.
Figure 7A:
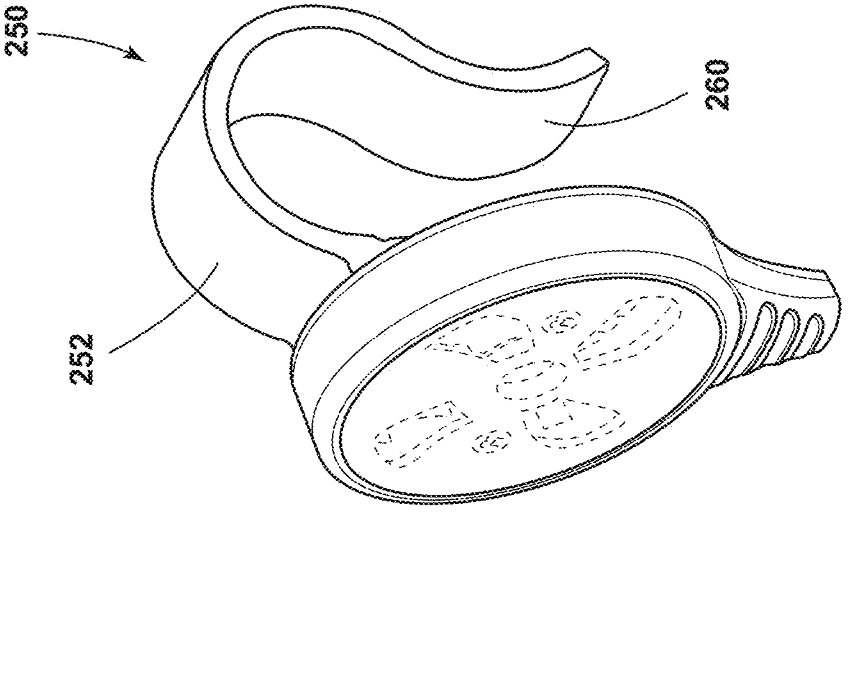
FIG. 7A is a top front perspective view of another connection feature for a medical equipment status indicator of the present disclosure.
Figure 7C:
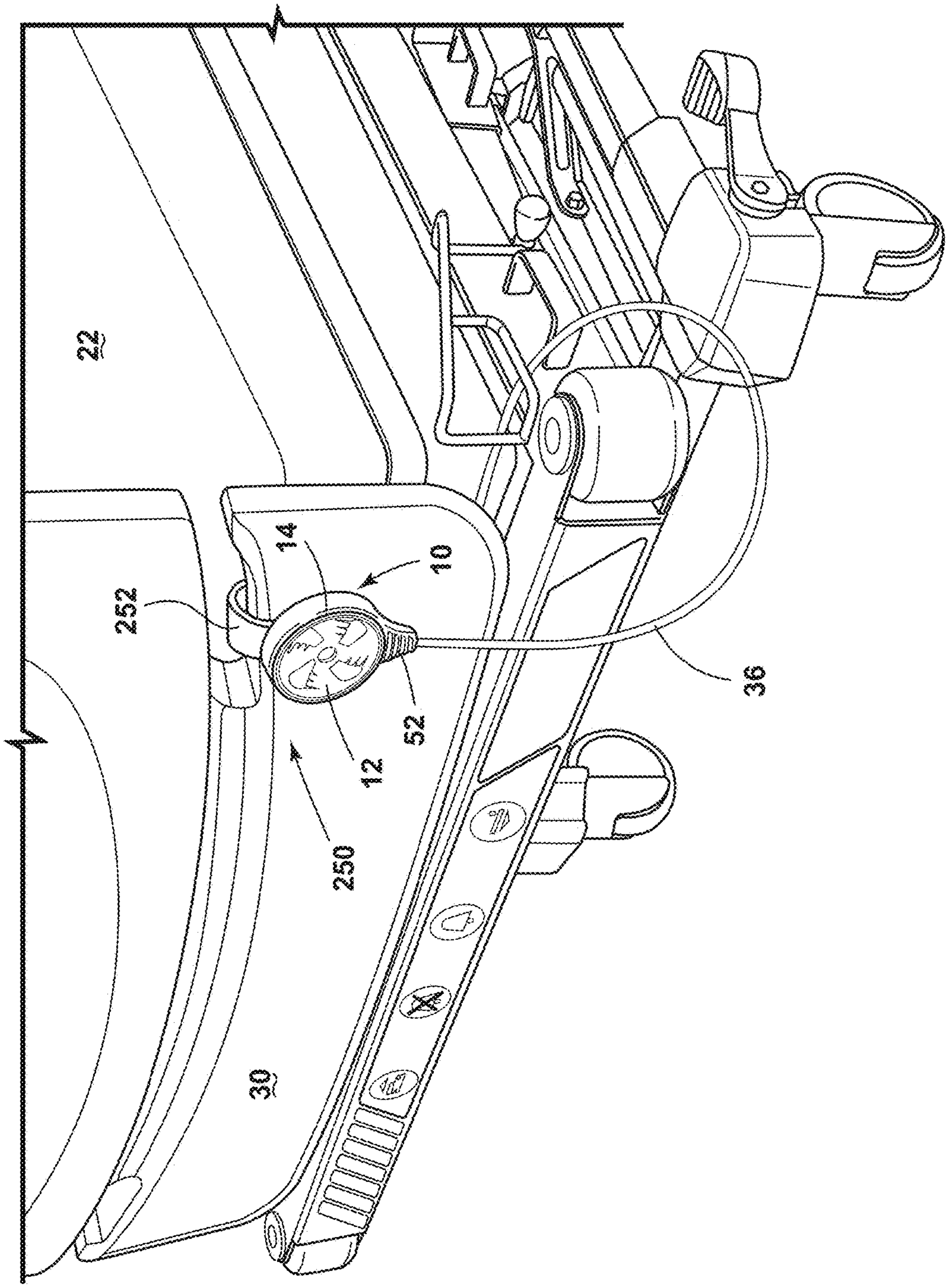
FIG. 7C illustrates the connection feature of FIG. 7B, securing the medical equipment status indicator to a footboard of a hospital bed.

With reference now to FIGS. 7A and 7B, in another construction, a connection feature 250 includes a flexible hook 252. The flexible hook 252 includes mechanical fasteners 254 that are secured to a back side 256 of the housing 12 of the mattress state indicator 10 or to the housing 102 of the mattress state indicator 100. The flexible hook 252 includes a rounded body that works in a similar fashion to the spring steel clamp 172 set forth in FIGS. 5A and 5B. When removal of the mattress state indicator 10 (or the mattress state indicator 100) from the hospital bed 22 is desired, a caregiver simply pulls a lower end 260 of the flexible hook 252 away from the mattress state indicator 10 (or the mattress state indicator 100) and repositions the mattress state indicator 10 (or the mattress state indicator 100) on a different location of the hospital bed 22 or removes the mattress state indicator from the hospital bed 22 altogether. FIG. 7C clearly illustrates the mattress state indicator 10 utilizing the flexible hook 252 and connecting the mattress state indicator 10 to a lower portion of the footboard 30 of the hospital bed 22.

Figure 8:
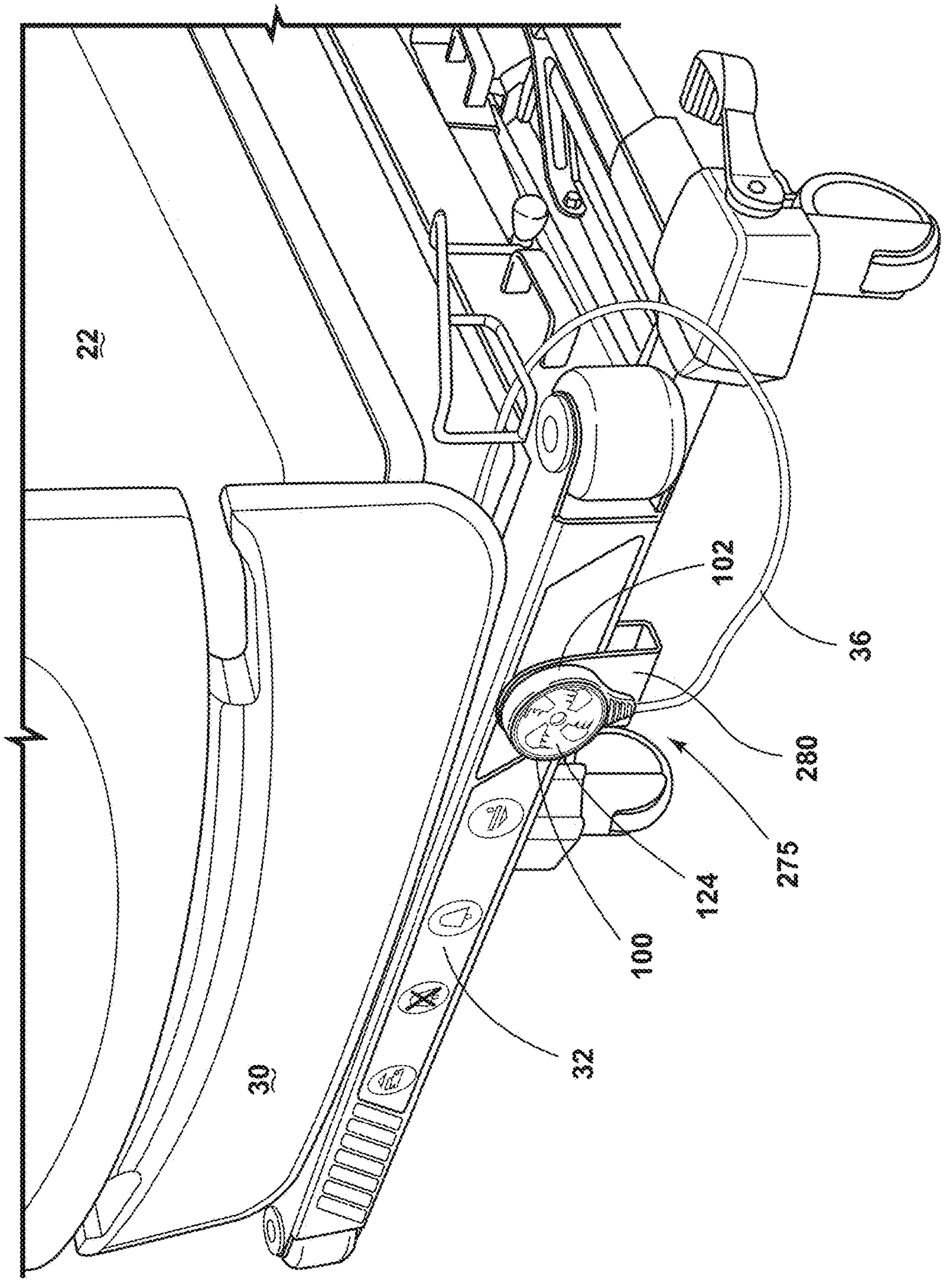
FIG. 8 illustrates another connection feature used to secure a medical equipment status indicator to a hospital bed.

With reference now to FIG. 8, connection feature 275 is illustrated which includes a lower bracket 280 that may also be secured on the mattress state indicator 100, as shown, or the mattress state indicator 10 to the lower frame 32 of the hospital bed 22. In this instance, the lower bracket 280 may be mechanically fastened to the mattress state indicator 100, adhered to the mattress state indicator 100 (or the mattress state indicator 10), or magnetically coupled to mattress state indicator 100 (or the mattress state indicator 10), for example. It will generally be contemplated that the lower bracket 280 will be mechanically fastened to the lower frame 32 of the hospital bed 22.

Figure 9:
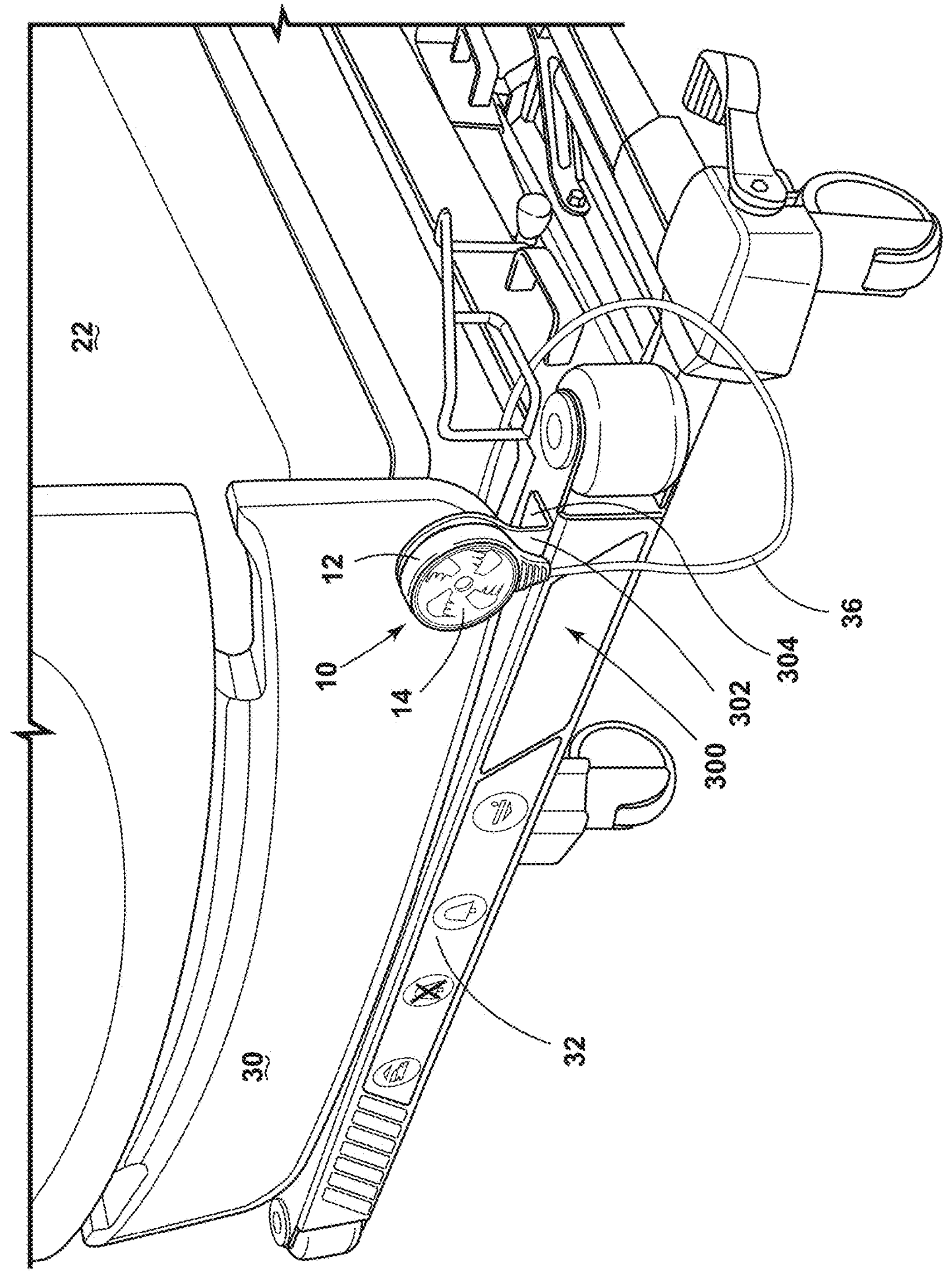
FIG. 9 illustrates yet another connection feature that can be used to secure a medical equipment status indicator to a hospital bed.

With reference now to FIG. 9, another connection feature 300 is illustrated which includes a bracket 302, which is disposed above the lower frame 32 of the hospital bed 22. The bracket 302 works in a similar fashion to that set forth in FIG. 8, and includes a base 304 operably coupled with the frame 32. The bracket 302 may interface with the mattress state indicator 10 (or the mattress state indicator 100) via magnet, adhesive, mechanical fasteners, etc.

Figure 10:
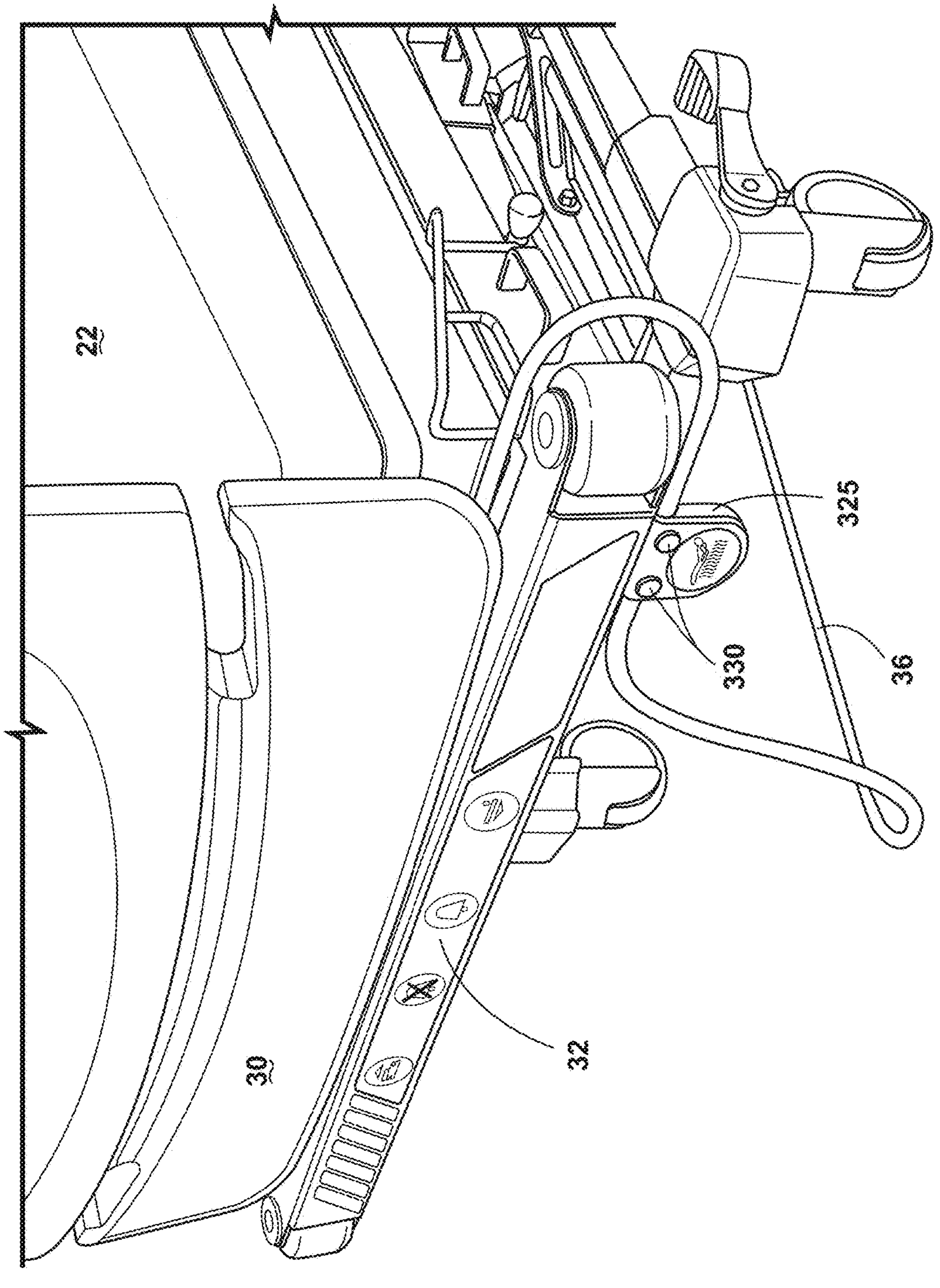
FIG. 10 illustrates yet another connection feature that can be used to secure a medical equipment status indicator to a hospital bed.

With reference now to FIG. 10, another connection feature 325 includes magnets 330 that are disposed on a top portion of the mattress state indicator. In this instance, the mattress state indicator is secured to the lower frame 32 of the hospital bed 22 by magnetically coupling the top portion of the mattress state indicator proximate the magnets 330 rather than, for example, by the back side 256 of the housing 12 of the mattress state indicator 10. Consequently, the mattress state indicator will frequently be placed underneath the lower frame 32 or other metallic structure of the hospital bed 22 so as to provide a line of sight to the front side of the housing 12 which includes the display 14 of the mattress state indicator.

Figure 11:
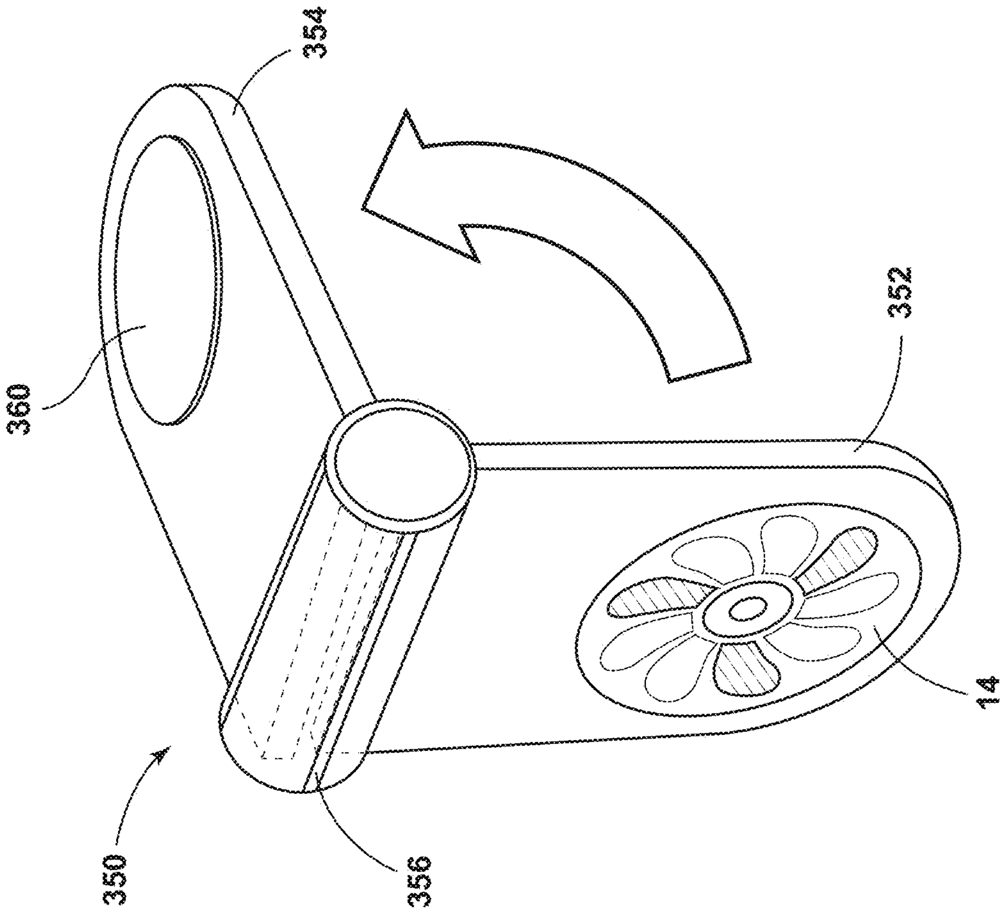
FIG. 11 is a top perspective view of a medical equipment status indicator of the present disclosure.

With reference now to FIG. 11, in another aspect of the present disclosure, a connection feature 350 for use with a mattress state indicator includes first and second arms 352, 354 that are connected by a rotary friction joint 356. The rotary friction joint 356 may be spring loaded to urge the first and second arms 352, 354 together. A magnet 360 is disposed on both sides of the second arm 354 and is configured to secure the mattress state indicator to the hospital bed 22 via a magnetic coupling. The first arm 352 is integral with the mattress state indicator and shows the display 14 which is configured to provide information to a caregiver regarding the status of the mattress state indicator.

The present disclosure sets forth various constructions for a mattress state indicator. The mattress state indicator is generally configured to provide visual information to a caregiver. However, it is also contemplated that the mattress state indicator may also provide audible information (a sound or alert) that may provide information to a caregiver related to the operation state of the mattress of the hospital bed 22. The display 14 may also include an interface configured to receive input from a user. The display 14 may also include a graphical user interface with a dynamic icon that may blink at a predetermined rate. For example, the display 14 may include a multitude of visual indicia 16 that can be lit in sequence thereby giving the appearance of a rotating fan to a caregiver. In this instance, the rotating fan would indicate that the mattress operation state is active. It is also contemplated that the dynamic icon may be lit in a predetermined sequence of long and short blinks to identify to a caregiver failure of the mattress to operate effectively. For example, the blink rate may indicate the existence of a product failure or an otherwise compromised state of the mattress to function as intended.

In addition, the visual indicia 16 may also be operable to provide different color light outputs depending on the mattress operation state. For example, if there is an error or if attention needs to be brought to the operation state of the mattress, the visual indicia 16 may illuminate in an amber color. The display 14 or the display 124 may include an icon that illuminates in a first color to indicate that the mattress is in a first operation state. Similarly, the icon of the display 14 or the display 124 may illuminate in a second color to indicate that the mattress is in a second operation state. If the display 14 or the display 124 is not illuminated at all, then it will be understood that the mattress is not currently operating. It will be understood by one having ordinary skill in the art that a variety of different visual indicators may be available and provided on the display 14.

In addition, the mattress state indicator 10 or the mattress state indicator 100 may be backlit and have a varying output depending on whether the display 14 is in a standby mode condition or in an active condition. Stated differently, the display 14 of the mattress state indicator 10 or the display 124 of the mattress state indicator 100 may be backlit by the light source 18 operable between a standby condition and an active condition brightness. Moreover, the display 14 may include various input capabilities. For example, it is generally contemplated that activation or deactivation of a mattress fan may be set at the mattress state indicator. In this instance, the display 14 may include a capacitive touch or push-push button assembly, for example, that allows a caregiver to activate or deactivate the mattress fan. Other interface options are also possible.

According to another aspect of the present disclosure, a mattress state indicator includes a housing. The mattress state indicator also includes a display supported by the housing. The display is configured to provide visual indicia of a mattress operation state of a mattress. The display includes a light source disposed proximate the display. A connection feature is engaged with the housing. The connection feature is configured to couple the housing with a bed.

According to still another aspect of the present disclosure, a connection feature includes a magnet that is disposed in a housing.

According to yet another aspect of the present disclosure, a cord couples a housing to a bed that provides electrical communication between a display and a controller of the bed.

According to another aspect of the present disclosure, a complementary connection feature is disposed within a bed.

According to another aspect of the present disclosure, a complementary connection feature is embedded within a footboard of a bed.

According to yet another aspect of the present disclosure, a display includes an interface configured to receive input from a user.

According to still another aspect of the present disclosure, a display includes an icon that illuminates in a first color to indicate that a mattress is in a first operation state and illuminates in a second color to indicate that the mattress is in a second operation state.

According to another aspect of the present disclosure, a display includes a graphical user interface and a dynamic icon that blinks at a predetermined rate.

According to still another aspect of the present disclosure, a dynamic icon blinks in a sequence of long and short blinks to identify a mattress operation state failure.

According to yet another aspect of the present disclosure, a display is backlit by a light source. The light source is operable between an active condition brightness and a standby condition brightness.

According to another aspect of the present disclosure, a display communicates wirelessly with a controller that is configured to adjust an operation state of the mattress.

According to still another aspect of the present disclosure, a connection feature operably couples a housing with a footboard of the bed.

According to still yet another aspect of the present disclosure, a connection feature includes a bracket that operably couples a housing to a bed.

According to another aspect of the present disclosure, a mattress state indicator includes a housing. A display is supported by the housing and is configured to provide visual indicia of a mattress operation state of a mattress. The display includes a light source disposed proximate the display. A bracket is engaged with the housing and includes a clamp that applies a compressive force against a portion of a bed.

According to yet another aspect of the present disclosure, a clamp is a spring steel clamp that includes first and second arms. One of the first arm and the second arm includes a pliable engagement member on an inside surface and a magnetic member on an outside surface.

According to another aspect of the present disclosure, a clamp includes a threaded engagement member that is configured to draw first and second arms of the clamp together.

According to still another aspect of the present disclosure, a clamp includes first and second threaded dowels that extend through the first and second arms, which receive a threaded engagement member.

According to yet another aspect of the present disclosure, a mattress state indicator assembly includes a housing and a display that provides visual indicia of an operation state of a mattress. The display communicates wirelessly with a controller of a bed that controls the operation state of the mattress. A connector is disposed within the housing and engages a complementary connector disposed within the bed.

According to still another aspect of the present disclosure, a complementary connector is embedded within a footboard of the bed.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A mattress state indicator comprising:

a housing;

a display supported by the housing and configured to provide visual indicia of a rotating fan indicative of an operation state of a mattress, wherein the display includes a light source disposed proximate the display, and further wherein the display provides visual indication of operation of an air movement fan of the mattress but is free of an interactive interface;

a magnetic connection feature disposed on the housing, the magnetic connection feature configured to magnetically engage a complementary feature on a portion of a bed; and a clamp that includes first and second arms, and wherein one of the first arm and the second arm includes a pliable engagement member on an inside surface and a magnetic member on an outside surface, and wherein the first arm is longer than the second arm.

2. The mattress state indicator of claim 1, wherein the clamp includes a threaded engagement member configured to draw first and second arms of the clamp together.

3. The mattress state indicator of claim 2, wherein the clamp includes first and second threaded dowels that extend through the first and second arms, and which receive the threaded engagement member.

* * * * *